United States Patent

Glandorf

[11] Patent Number: 5,820,853
[45] Date of Patent: Oct. 13, 1998

[54] ORAL COMPOSITIONS FORMING A COACERVATE GEL

[75] Inventor: William Michael Glandorf, Mason, Ohio

[73] Assignee: The Procter & Gamble Company, Cincinnati, Ohio

[21] Appl. No.: 826,458

[22] Filed: Mar. 27, 1997

[51] Int. Cl.$^6$ .............................. A61K 7/16; A61K 7/18
[52] U.S. Cl. ................... 424/52; 424/49; 424/57
[58] Field of Search ......................... 424/49–88

[56] References Cited

U.S. PATENT DOCUMENTS

| | | | |
|---|---|---|---|
| 3,839,220 | 10/1974 | Barchas | 252/305 |
| 4,071,614 | 1/1978 | Grimm | 424/49 |
| 4,211,341 | 7/1980 | Weyn | 222/94 |
| 4,348,378 | 9/1982 | Kosti | 424/49 |
| 4,401,648 | 8/1983 | Piechota, Jr. | 424/49 |
| 4,487,757 | 12/1984 | Kiozpeoplou | 424/49 |
| 4,837,007 | 6/1989 | Duckworth et al. | 424/49 |
| 4,988,500 | 1/1991 | Hunter et al. | 424/53 |
| 5,000,941 | 3/1991 | Chernack | 424/53 |
| 5,037,637 | 8/1991 | Gaffar et al. | 424/52 |
| 5,077,051 | 12/1991 | Gallopo et al. | 424/435 |
| 5,126,061 | 6/1992 | Michael | 252/86 |
| 5,256,402 | 10/1993 | Prencipe et al. | 424/53 |
| 5,403,578 | 4/1995 | Gordon | 424/53 |
| 5,460,817 | 10/1995 | Langley et al. | 424/408 |
| 5,476,660 | 12/1995 | Somasundaran et al. | 424/401 |
| 5,565,190 | 10/1996 | Santalucia et al. | 424/53 |
| 5,599,525 | 2/1997 | Hsu et al. | 424/53 |
| 5,639,475 | 6/1997 | Bettman et al. | 424/466 |

Primary Examiner—Shep K. Rose
Attorney, Agent, or Firm—Angela Marie Stone; Mary Catherine Hentz; Douglas C. Mohl

[57] ABSTRACT

The present invention relates to a dentifrice formulation comprising first and second dentifrice compositions and to a dentifrice formulation that is a single dentifrice composition. The first dentifrice composition or the single dentifrice composition will comprise from about 0.1% to about 10% of a surfactant selected from the group consisting of anionic surfactants, cationic surfactants, amphoteric surfactants, and mixtures thereof; from about 0.1% to about 10% of a charged polymer; and from about 80% to about 99% of one or more aqueous carriers; wherein the charged polymer is diluted to form a charged polymer slurry and the pH of the charged polymer slurry is from about 1.5 to about 10, the charged polymer slurry is combined with the anionic, cationic, or amphoteric surfactant to form a coacervate gel, and the coacervate gel is then combined with the one or more aqueous carriers to form the dentifrice composition. The present invention also relates to a method of making a dentifrice composition containing a coacervate gel, comprising the steps of diluting from about 0.1% to about 10% of a charged polymer to form a charged polymer slurry, the charged polymer slurry having a pH of from about 1.5 to about 10; combining the charged polymer slurry with from about 0.1% to about 10% of a surfactant selected from the group consisting of anionic surfactants, cationic surfactants, amphoteric surfactants, and mixtures thereof, to form a coacervate gel; and combining the coacervate gel with from about 80% to about 99% of one or more aqueous carriers to form the dentifrice composition.

18 Claims, No Drawings

ORAL COMPOSITIONS FORMING A COACERVATE GEL

BACKGROUND OF THE INVENTION

The present invention relates to dentifrice formulations which contain a coacervate gel. The coacervate gel is formed by combining an anionic, cationic, and/or amphoteric surfactant with a charged polymer. The coacervate gel is then combined with the additional carrier materials to form the dentifrice composition. The dentifrice formulation may contain two separate dentifrice compositions or a single dentifrice composition.

Coacervate gels are known in the art. Coacervate gels are commonly formed in shampoos and other soaps. Coacervate gels are used to deposit active substances on a target surface. Examples include U.S. Pat. No. 5,476,660, to Somasundaran et al., issued Dec. 19, 1995. Coacervate gels are also used to form microcapsules. Typically, the microcapsule will comprise perfumes, silica, or other substances to be deposited. An example of a microcapsule formed by a coacervate gel includes U.S. Pat. No. 5,126,061, issued Jun. 30, 1992, to Michael. In the present invention, a coacervate gel is formed but it is not used to microencapsulate a substance.

Also known in the art are the polymers used to form the coacervate gels. Although these polymers are used in dentifrices, the polymer used are neutralized and do not remain charged. For example, U.S. Pat. No. 4,988,500 to Hunter et al., issued Jan. 29, 1991, describes the use of a carboxyvinyl polymer in a dentifrice. In the present invention, the polymer will remain charged to form a coacervate gel with the surfactant.

It is known that dentifrice aesthetics can be improved by optimizing the foaming and product consistency. The present inventor has discovered that a dentifrice with improved sensory attributes can be made by forming a coacervate gel. By forming a coacervate gel in the dentifrice composition, the dentifrice and foam have a creamier consistency and a slick, smooth teeth feeling is achieved. Additionally, the dentifrice may also provide a longer lasting flavor. Therefore, it is an object of the present invention to provide stable dentifrice formulations comprising a coacervate gel. The dentifrice formulation may be a single composition with a coacervate gel or a dual phase composition in which one or both dentifrice compositions comprise a coacervate gel. It is also an object of the present invention to provide a method of making a dentifrice formulation with a coacervate gel.

These and other objects of the present invention will become readily apparent from the detailed description which follows.

All percentages and ratios used herein are by weight of the specific dentifrice composition and not of the overall dentifrice formulation that is delivered, unless otherwise specified. All measurements are made at 25° C., unless otherwise specified.

SUMMARY OF THE INVENTION

The present invention relates to a dentifrice formulation comprising first and second dentifrice compositions and to a dentifrice formulation that is a single dentifrice composition. The first dentifrice composition or the single dentifrice composition will comprise from about 0.1% to about 10% of a surfactant selected from the group consisting of anionic surfactants, cationic surfactants, amphoteric surfactants, and mixtures thereof; from about 0.1% to about 10% of a charged polymer; and from about 80% to about 99% of one or more aqueous carriers; wherein the charged polymer is diluted to form a charged polymer slurry and the pH of the charged polymer slurry is from about 1.5 to about 10, the charged polymer slurry is combined with the anionic, cationic, or amphoteric surfactant to form a coacervate gel, and the coacervate gel is then combined with the one or more aqueous carriers to form the dentifrice composition. The present invention also relates to a method of making a dentifrice composition containing a coacervate gel, comprising the steps of diluting from about 0.1% to about 10% of a charged polymer to form a charged polymer slurry, the charged polymer slurry having a pH of from about 1.5 to about 10; combining the charged polymer slurry with from about 0.1% to about 10% of a surfactant selected from the group consisting of anionic surfactants, cationic surfactants, amphoteric surfactants, and mixtures thereof, to form a coacervate gel; and combining the coacervate gel with from about 80% to about 99% of one or more aqueous carriers to form the dentifrice composition.

DETAILED DESCRIPTION OF THE INVENTION

The dentifrice formulation of the present invention may be in the form of a toothpaste or dentifrice. The term "dentifrice formulation" as used herein means the total dentifrice that is delivered to the oral surfaces. The dentifrice formulation may be a combination of the two or more dentifrice compositions or may be a single dentifrice composition. The dentifrice formulation is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side or may be a single composition.

The term "dispenser", as used herein, means any pump, tube, or container suitable for dispensing dentifrice.

The term "aqueous carrier" as used herein means any safe and effective materials for use in the compositions of the present invention. Such materials include alkali metal bicarbonate salts, calcium peroxide, abrasive polishing materials, propylene glycol, acidic compounds, buffering agents, polyoxyethylene, thickening materials, humectants, water, surfactants, titanium dioxide, flavor system, coolants, sweetening agents, xylitol, coloring agents, antimicrobial agents, and mixtures thereof.

The present compositions comprise essential components, as well as optional components. The essential and optional components of the compositions of the present invention are described in the following paragraphs.

Surfactants

Anionic, cationic, and/or amphoteric surfactants are required in the present invention. Suitable surfactants, commonly referred to as sudsing agents, are those which are reasonably stable and foam through a wide pH range. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate.

Preferred cationic surfactants useful in the present invention can be broadly defined as derivatives of aliphatic quaternary ammonium compounds having one long alkyl chain containing from about 8 to 18 carbon atoms. Suitable cationic surfactants include ethoxylated fatty amines, fatty ammonium chlorides, fatty pyridinium chlorides, fatty dimethylamines, fatty dimethylamine lactates, and mixture thereof. Specific cationic surfactants include lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, and cetyl pyridinium fluoride. The quaternary ammonium fluorides are described in U.S. Pat. No. 3,535,421, Oct. 20, 1970, to Briner et al., herein incorporated by reference. Certain cationic surfactants, such as chlorhexidine, can also act as antimicrobials in the compositions.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed, as well as mixtures of anionic, cationic, and/or amphoteric surfactants.

Many surfactants suitable for use are disclosed by Gieske et al., U.S. Pat. No. 4,051,234, issued Sep. 27, 1977, incorporated herein by reference in its entirety. The present composition typically comprises one or more surfactants at a level of from about 0.1% to about 10%, preferably from about 0.2% to about 8%, and most preferably from about 0.25% to about 6%, by weight of the composition.

Charged Polymer

The present invention also comprises a charged polymer. The charged polymer will be anionic or cationic. Preferably, the charge of the polymer should be opposite the charge of the surfactant if an amphoteric surfactant is not present by itself or in combination with another surfactant. For example, if the charged polymer is anionic, the surfactants may be amphoteric; cationic; amphoteric and cationic; amphoteric and anionic; or amphoteric, anionic, and cationic. Suitable cationic polymers include cationically modified guar gum, polyquaternary amines, and polyacrylamides. Suitable anionic polymers include polyacrylic acids, polyvinyl acetates, polymaleic acid, polycarbonates, polysulfonates, and mixtures thereof. Additional anionic polymeric polycarboxylates, such as Gantrez, are described in U.S. Pat. No. 5,037,637 to Gaffar et al, issued Aug. 6, 1991, incorporated herein by reference in its entirety including all references incorporated into this reference. The preferred anionic polymer is a carboxyvinyl polymer. Carboxyvinyl polymers are described in U.S. Pat. No. 2,798,053 to Brown, issued Jul. 2, 1957, incorporated herein by reference. Carboxyvinyl polymers are provided by B. F. Goodrich Company as Carbopol 934, 940, 941, 946, and 956. Mixtures of charged polymers can also be employed.

The present composition typically comprises a charged polymer at a level of from about 0.1% to about 10%, preferably from about 0.2% to about 8%, and most preferably from about 0.25% to about 6%, by weight of the dentifrice composition.

Coacervate Gel

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries,* Vol. 106, April 1991, pp 49–54, C. J. van Oss, "Coacervation, Complex-Coacervation and Flocculation", *J. Dispersion Science and Technology,* Vol. 9 (5,6), 1988–89, pp 561–573, and D. J. Burgess, "Practical Analysis of Complex Coacervate Systems", *J. of Colloid and Interface Science,* Vol. 140, No. 1, November 1990, pp 227–238, which descriptions are incorporated herein by reference.

The coacervate gel of the present invention comprises anionic, cationic, and/or amphoteric surfactants and a charged polymer. The coacervate gel is formed by combining the charger polymer with the surfactant. Preferably, the charged polymer is contained in a slurry. The charged polymer slurry will have a pH of from about 1.5 to about 10. An anionic polymer slurry will have a pH of from about 1.5 to about 7 and preferably from about 1.5 to about 4.5. A cationic polymer slurry will have a pH of from about 7 to about 10 and preferably from about 7.5 to about 9. The slurry may comprise humectants and/or water. Preferred humectants include glycerin and sorbitol. The ratio of charged polymer to humectant is from about 1:20 to about 1:100, preferably from about 1:30 to about 1:60. The charged polymer slurry is then combined with the surfactant. This forms the coacervate gel. A coacervate gel formed by an anionic polymer will have a pH of from about 3 to about 7, preferably from about 4.5 to about 6.5, and more preferably from about 4.5 to about 6.0. A coacervate gel formed by a cationic surfactant will have a pH of from about 7 to about 9 and preferably from about 8 to about 8.5. After the coacervate gel is formed, it may be neutralized with a buffering agent to form the dentifrice composition. The final pH of the dentifrice composition will be from about 4 to about 8.5. The final pH of a dentifrice composition containing a coacervate gel made with an anionic polymer will be from about 5 to about 6.

The coacervate gel may additionally comprise a flavor system or other hydrophobic species. If a hydrophobic species is present, it will be emulsified with the surfactant. The emulsified surfactant and hydrophobic species will then be added to the charged polymer slurry to form the coacervate gel.

Fluoride Ion Source

The first and/or second dentifrice compositions or the single dentifrice composition of the present invention may incorporate a soluble fluoride ion source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety. The fluoride ion source should be capable of providing from about 50 ppm to about 3500 ppm, and preferably from about 500 ppm to about 3000 ppm of free fluoride ions.

Tartar Control Agents

The present invention may include a tartar control agent. The tartar control agent may be present in the first or second dentifrice compositions, both compositions, or in the single dentifrice composition. The tartar control agent may be any materials known to be effective in reducing calcium phosphate mineral deposition related to calculus formation. The preferred tartar control agent is selected from the group consisting of a polyphosphate source, tripolyphosphate source, a pyrophosphate salt, and mixtures thereof.

The pyrophosphate salts useful in the present compositions include the di and tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. Compositions comprising pyrophosphate typically containing from about 1% to about 15%, preferably from about 2% to about 10%, and most preferably from about 2% to about 8%, by weight of the composition. The pyrophosphate salts are described in U.S. Pat. Nos. 4,515,772, issued May 7, 1985, and 4,885,155, issued Dec. 5, 1989, both to Parran et al., incorporated herein by reference in their entirety, including references incorporated into these references.

The present invention may include a polyphosphate source. A polyphosphate is generally understood to consist of two or more phosphate molecules arranged primarily in a linear configuration, although some cyclic derivatives may be present. The inorganic polyphosphate salts desired include sodium tripolyphosphate, tetrapolyphosphate, and hexametaphosphate, among others. Polyphosphates larger than tetrapolyphosphate usually occur as amorphous glassy materials. Preferred are polyphosphates manufactured by FMC Corporation which are commercially known as Sodaphos (n≈6), Hexaphos (n≈13), and Glass H (n≈21). The polyphosphate source will typically comprise from about 0.5% to about 20%, preferably from about 4% to about 15%, more preferably from about 6% to about 10%, and most preferably from about 7% to about 9%, by weight of the dentifrice composition.

The phosphate sources are described in more detail in Kirk & Othmer, *Encyclopedia of Chemical Technology*, Fourth Edition, Volume 18, Wiley-Interscience Publishers (1996), pages 685–707, incorporated herein by reference in its entirety, including all references incorporated into Kirk & Othmer. Optional agents to be used in place of or in combination with the polyphosphate or pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

Aqueous Carriers

In preparing the present compositions, it is desirable to add one or more aqueous carriers to the dentifrice compositions. Such materials are well known in the art and are readily chosen by one skilled in the art based on the physical and aesthetic properties desired for the compositions being prepared. Aqueous carriers typically comprise from about 10% to about 99%, preferably from about 45% to about 98%, and more preferably from about 75% to about 95%, by weight of the dentifrice composition.

Alkali Metal Bicarbonate Salt

The dentifrice compositions of the present invention may also include an alkali metal bicarbonate salt. The alkali metal bicarbonate salt may be present in one or both dentifrice composition or in the single dentifrice composition. Sodium bicarbonate, also known as baking soda, is the preferred alkali metal bicarbonate salt. The present composition may contain from about 6% to about 50%, preferably from about 7% to about 30%, more preferably from about 8% to about 20%, and most preferably from about 8% to about 18% of an alkali metal bicarbonate salt, by weight of the dentifrice composition.

Calcium Peroxide

The present invention may include calcium peroxide in any of the dentifrice compositions. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Abrasive Polishing Materials

An abrasive polishing material may also be included in the dentifrice compositions. The abrasive polishing material contemplated for use in the compositions of the present invention can be any material which does not excessively abrade dentin. Typical abrasive polishing materials include silicas including gels and precipitates; aluminas; phosphates including orthophosphates, polymetaphosphates, and insoluble pyrophosphates; and mixtures thereof. Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, and in Rice, U.S. Pat. No. 5,589,160, issued Dec. 31, 1996, incorporated herein by reference. Silica abrasives described in U.S. patent application Ser. Nos., 08/434,147 and 08/434,154, both filed May 2, 1995, are also herein incorporated by reference. The abrasive in the toothpaste compositions described herein is generally present at a level of from about 6% to about 70% by weight of the composition. Preferably, toothpastes contain from about 10% to about 50% of abrasive, by weight of the dentifrice composition.

Propylene Glycol

The dentifrice compositions may also comprise propylene glycol. The propylene glycol is suitable for use on the skin and mucosal surfaces such as in the oral cavity. The first dentifrice composition may contain from about 0.5% to about 30%, preferably from about 1% to about 20%, and more preferably from about 2% to about 15% of propylene glycol, by weight of the dentifrice composition.

Acidic Compound

The dentifrice compositions of the present invention may incorporate an acidic compound. The acidic compound may be organic or inorganic. The acidic compound may be any material which will be a proton donor that is capable of neutralizing bicarbonate. Acidic compounds suitable for use include carboxylic acids, phosphoric acids, alpha-hydroxy acids, sulfonic acids, and mixture thereof. Specific acids include citric acid, malic acid, alginic acid, succinic acid, lactic acid, tartaric acid, glycolic acid, adipic acid, potassium bitartrate acid, acid sodium citrate, phosphoric acid, boric acid, and acid phosphate and pyrophosphate salts. A blend of acids are preferred. Citric acid and malic acid are preferred. Acid anhydrides and acid salts of the above acids may also be used. Suitable salts include mono or disodium salts of citric acid, mono sodium salts of malic acid, and mixtures thereof. The second dentifrice composition may contain from about 0.5% to about 20%, preferably from about 1% to about 15%, and more preferably from about 4% to about 12% of an acidic compound, by weight of the dentifrice composition.

Buffering Agent

The dentifrice compositions may contain a buffering agent. Buffering agents, as used herein, refer to agents that can be used to adjust the pH of the compositions. The buffering agents suitable include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, sodium acid pyrophosphate, sodium citrate, and sodium malate. Buffering agents are used at a level of from about 0.1% to about 30%, preferably from about 1% to about 10%, and more preferably from about 1.5% to about 3%, by weight of the dentifrice composition.

Polyoxyethylene

The present invention may include a polyoxyethylene. The polyoxyethylene will increase the amount of foam and the thickness of the foam. Polyoxyethylene is also commonly known as polyethylene glycol ("PEG") or polyethylene oxide. The polyoxyethylenes suitable for this invention will have a molecular weight of from about 200,000 to about 7,000,000. Preferably, the molecular weights will be from about 600,000 to about 2,000,000, and more preferably from about 800,000 to about 1,000,000. "Polyox" is the tradename for the high molecular weight polyoxyethylene produced by Union Carbide. The polyoxyethylene is present in an amount of from about 0.1% to about 8%, preferably from about 0.2% to about 5%, and more preferably from about 0.3% to about 2%, by weight of the dentifrice composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, and other edible polyhydric alcohols. The polyethylene glycol may have a molecular weight of from about 200 to about 7000. The humectant generally comprises from about 0% to 70%, and preferably from about 15% to 55%, by weight of the dentifrice composition.

Water employed in the preparation of commercially suitable dentifrice compositions should preferably be of low ion content and free of organic impurities. Water will generally comprise from about 5% to about 70%, and preferably from about 10% to about 50%, by weight of the composition herein. Alternatively, the dentifrice compositions may comprise a lower level of water, generally from about 5% to about 20%, preferably from about 7% to about 14%, and more preferably from about 7% to about 12%, by weight of the dentifrice composition. The lower level of water is preferred in compositions comprising polyphosphates. The amounts of water include the free water which is added plus that which is introduced with other materials, such as with sorbitol, silica, surfactant solutions, and/or color solutions.

The present compositions may also comprise additional surfactants, also commonly referred to as sudsing agents. The additional surfactant may be nonionic. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), and mixtures of such materials. Many suitable nonionic surfactants are disclosed by Gieske et al., U.S. Pat. No. 4,051,234, issued Sep. 27, 1977, incorporated herein by reference in its entirety. The present composition may comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. A flavor system is generally used in the compositions at levels of from about 0.001% to about 5%, by weight of the composition.

Coolants may also be part of the flavor system or added separately to the composition. Preferred coolants in the present compositions are the paramenthan carboxyamide agents such as N-ethyl-p-menthan-3-carboxamide (known commercially as "WS-3"), menthol, 3-1-menthoxypropane-1,2-diol ("TK-10"), menthone glycerol acetal ("MGA"), menthyl lactate, and mixtures thereof. A coolant is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents and water soluble antimicrobials, such as quaternary ammonium salts and bis-biquanide salts, among others. Triclosan monophosphate is an additional water soluble antimicrobial agent. Other compounds are bis[4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 1.5%, by weight of the dentifrice composition.

The dentifrice formulation may contain a first and second dentifrice composition or a single dentifrice composition. If there are two dentifrice compositions, the first and second dentifrice compositions will be physically separated in a dentifrice dispenser. The dentifrice compositions may be a paste, gel, or any configuration or combination thereof. It is preferred that the first dentifrice composition be a gel and the second dentifrice composition be a paste. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. Nos. 4,687,663, issued Aug. 18, 1987; and 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the dentifrice formulation may be delivered from a kit containing two separate dispensers which are used to deliver two dentifrice compositions that are both used simultaneously.

Method of Treatment

The method of treatment herein comprises contacting the dental enamel surfaces in the mouth with the dentifrice compositions according to the present invention.

EXAMPLES & METHOD OF MANUFACTURING

The following examples further describe and demonstrate embodiments within the scope of the present invention. These examples are given solely for the purpose of illustration and are not to be construed as limitations of the present invention as many variations thereof are possible without departing from the spirit and scope.

Example I

| First Dentifrice Composition | | Second Dentifrice Composition | |
| --- | --- | --- | --- |
| Ingredient | Wt. % | Ingredient | Wt. % |
| Sodium Fluoride | 0.24 | Color | 0.30 |
| Water | 12.00 | Water | 50.00 |
| Flavor | 1.00 | Flavor | 1.00 |
| Sorbitol[c] | 58.36 | Glycerin | 40.26 |
| Titanium Dioxide | 0.50 | Carbopol | 2.80 |
| Xanthan Gum | 0.50 | Sodium Hydroxide[b] | 1.00 |
| Sodium Alkyl Sulfate[a] | 4.00 | Sodium Saccharin | 0.40 |
| Silica | 20.00 | Sodium Alkyl Sulfate[a] | 3.00 |
| Polyethylene Glycol | 3.00 | Sodium Fluoride | 0.24 |
| Sodium Saccharin | 0.40 | Polyoxyethylene | 1.00 |

[a] 27.9% solution
[b] 50% solution
[c] 70% solution

The first dentifrice composition is prepared as follows. Start by mixing the sodium fluoride and saccharin in water. Disperse the xanthan gum in the sorbitol before adding to the mixture. Add the polyethylene glycol. Add the flavor system, titanium dioxide, and sodium alkyl sulfate. Add the silica. Continue mixing until homogeneous. Mill and/or deareate the final product if desired for aesthetic preference.

For the second dentifrice composition, add the water, saccharin, color, and fluoride to the mixing vessel. Heat to at least 40° C. Premix the Carbopol and polyoxyethylene in the glycerin. Add this premix to the mixing vessel and mix well. Premix the flavor and sodium alkyl sulfate until uniform in color. Add this premix to the mixing vessel and mix well. Add the sodium hydroxide to the mixture and continue to mix until homogeneous.

Example II

| First Dentifrice Composition | | Second Dentifrice Composition | |
|---|---|---|---|
| Ingredient | Wt. % | Ingredient | Wt. % |
| Carboxymethylcellulose | 0.90 | Color | 0.30 |
| Water | 15.00 | Water | 29.06 |
| Flavor | 1.00 | Flavor | 1.00 |
| Glycerin | 24.76 | Triclosan | 0.60 |
| Calcium Peroxide | 1.00 | Carbopol | 2.50 |
| Sodium Fluoride | 0.24 | Sodium Hydroxide[b] | 1.00 |
| Sodium Alkyl Sulfate[a] | 4.00 | Sodium Saccharin | 0.40 |
| Silica | 22.00 | Sodium Alkyl Sulfate[a] | 2.00 |
| Sodium Carbonate | 2.00 | Betaine | 2.90 |
| Sodium Saccharin | 0.40 | Sorbitol[c] | 60.00 |
| Sodium Bicarbonate | 14.50 | Sodium Fluoride | 0.24 |
| Titanium Dioxide | 1.00 | | |
| Xanthan Gum | 0.20 | | |
| Polyethylene Glycol | 3.00 | | |
| Tetrasodium Pyrophosphate | 10.00 | | |

[a] 27.9% solution
[b] 50% solution
[c] 70% solution

The first dentifrice composition is prepared as follows. Place the water in a mixing vessel and add sodium fluoride and saccharin. Disperse the thickening agents, carboxymethylcellulose and xanthan gum, in the glycerin, before adding to the mixture. Add the polyethylene glycol. Next add the flavor system, titanium dioxide, and sodium alkyl sulfate. Add the sodium carbonate. Add the silica and then the sodium bicarbonate. Lastly, slowly add the tetrasodium pyrophosphate and finally the calcium peroxide. Continue mixing until homogeneous. Mill and/or deareate the final product if desired for aesthetic preference.

For the second dentifrice composition, add the water, saccharin, color, and fluoride to the mixing vessel. Heat to at least 40° C. Premix the Carbopol in the sorbitol. Add this premix to the mixing vessel and mix well. Premix the flavor, triclosan, and sodium alkyl sulfate until uniform in color and then add the betaine. Add this premix to the mixing vessel and mix well. Add the sodium hydroxide to the mixture and continue to mix until homogeneous.

Example III

| First Dentifrice Composition | | Second Dentifrice Composition | |
|---|---|---|---|
| Ingredient | Wt. % | Ingredient | Wt. % |
| Carboxymethylcellulose | 0.80 | Color | 0.30 |
| Water | 10.00 | Water | 48.00 |
| Flavor | 1.00 | Flavor | 0.80 |
| Glycerin | 8.00 | Glycerin | 39.76 |
| Sodium Fluoride | 0.24 | Carbopol | 2.60 |
| Sorbitol[c] | 25.06 | Sodium Hydroxide[b] | 1.00 |
| Sodium Alkyl Sulfate[a] | 4.00 | Sodium Saccharin | 0.40 |
| Silica | 15.00 | Sodium Alkyl Sulfate[a] | 2.00 |
| Sodium Carbonate | 2.00 | Betaine | 2.90 |
| Sodium Saccharin | 0.40 | Polyoxyethylene | 2.00 |
| Sodium Bicarbonate | 30.00 | Sodium Fluoride | 0.24 |
| Titanium Dioxide | 0.50 | | |
| Polyethylene Glycol | 3.00 | | |

[a] 27.9% solution
[b] 50% solution
[c] 70% solution

The first dentifrice composition is prepared as follows. Add the water, sodium fluoride, and saccharin to a mixing vessel. Disperse the thickening agents, carboxymethylcellulose, in the glycerin and sorbitol, before adding to the mixture. Add the polyethylene glycol, flavor system, and titanium dioxide. Add the sodium alkyl sulfate. Next add the sodium carbonate, silica, and then the sodium bicarbonate. Continue mixing until homogeneous. Mill and/or deareate the final product if desired for aesthetic preference.

For the second dentifrice composition, add the water, saccharin, color, and fluoride to the mixing vessel. Heat to at least 40° C. Premix the Carbopol and polyoxyethylene in the glycerin. Add this premix to the mixing vessel and mix well. Premix the flavor and sodium alkyl sulfate until uniform in color and then add the betaine. Add this premix to the mixing vessel and mix well. Add the sodium hydroxide to the mixture and continue to mix until homogeneous.

Example IV

| First Dentifrice Composition | | Second Dentifrice Composition | |
|---|---|---|---|
| Ingredient | Wt. % | Ingredient | Wt. % |
| Carboxymethylcellulose | 0.45 | Color | 0.30 |
| Water | 5.00 | Water | 48.00 |
| Flavor | 0.90 | Flavor | 0.80 |
| Glycerin | 34.00 | Glycerin | 38.44 |
| Xanthan Gum | 0.25 | Carbopol | 2.60 |
| Poloxamer | 3.00 | Sodium Hydroxide[b] | 1.00 |
| Sodium Alkyl Sulfate[a] | 4.00 | Sodium Saccharin | 0.40 |
| Silica | 19.00 | Sodium Alkyl Sulfate[a] | 2.00 |
| Sodium Carbonate | 2.00 | Betaine | 2.90 |
| Sodium Saccharin | 0.40 | Polyoxyethylene | 3.00 |
| Sodium Bicarbonate | 9.00 | Sodium Fluoride | 0.56 |
| Titanium Dioxide | 1.00 | | |
| Polyethylene Glycol | 3.00 | | |
| Glass H Polyphosphate | 10.00 | | |
| Propylene Glycol | 8.00 | | |

[a] 27.9% solution
[b] 50% solution

The first dentifrice composition is prepared as follows. Add the saccharin and water to a mixing vessel. Disperse the thickening agents, carboxymethyl cellulose and xanthan gum, in the glycerin. Add this mixture of dispersed thickening agents in glycerin to the mixing vessel and mix well. Add the flavor, Poloxamer, polyethylene glycol, propylene glycol, titanium dioxide, and sodium alkyl sulfate to the mixture and mix until homogeneous. Next add the sodium carbonate and the silica. After mixing, add the sodium bicarbonate. Finally add the polyphosphate. Continue stirring the mixture until homogeneous.

For the second dentifrice composition, add the water, saccharin, color, and fluoride to the mixing vessel. Heat to at least 40° C. Premix the Carbopol and polyoxyethylene in the glycerin. Add this premix to the mixing vessel and mix well. Premix the flavor and sodium alkyl sulfate until uniform in color and then add the betaine. Add this premix to the mixing vessel and mix well. Add the sodium hydroxide to the mixture and continue to mix until homogeneous.

Example V

| Ingredient | Weight % |
|---|---|
| Glycerin | 40.00 |
| Water | 49.76 |
| Betaine | 2.90 |
| Sodium Fluoride | 0.24 |
| Sodium Saccharin | 0.40 |

-continued

| Ingredient | Weight % |
| --- | --- |
| Sodium Alkyl Sulfate[a] | 2.00 |
| Flavor System | 0.80 |
| Color | 0.30 |
| Carbopol | 2.60 |
| Sodium Hydroxide[b] | 1.00 |

[a]27.9% solution
[b]50% solution

The dentifrice composition is prepared as follows. Add the water, saccharin, color, and fluoride to the mixing vessel. Heat to at least 40° C. Premix the Carbopol in the glycerin. Add this premix to the mixing vessel and mix well. Premix the flavor and sodium alkyl sulfate until uniform in color and then add the betaine. Add this premix to the mixing vessel and mix well. Add the sodium hydroxide to the mixture and continue to mix until homogeneous.

Example VI

| Ingredient | Weight % |
| --- | --- |
| Glycerin | 32.26 |
| Water | 38.00 |
| Sodium Fluoride | 0.24 |
| Sodium Saccharin | 0.40 |
| Silica | 20.00 |
| Sodium Alkyl Sulfate[a] | 4.00 |
| Flavor System | 0.80 |
| Color | 0.30 |
| JR-30M PolyQuat | 4.00 |

[a]27.9% solution

Examples VI is prepared as follows. Add the water, saccharin, color, and fluoride to the mixing vessel. Heat to at least 40° C. Premix the PolyQuat in the glycerin. Add this premix to the mixing vessel and mix well. Premix the flavor and sodium alkyl sulfate until uniform in color and add this premix to the mixing vessel. Add the silica to the mixture and continue to mix until homogeneous. Mill and/or deareate the final product if desired for aesthetic preference.

What is claimed is:

1. A dentifrice formulation contained in physically separated compartments of a dispenser, comprising:
   a. a first dentifrice composition comprising:
      (i) from about 0.1% to about 10% of a surfactant selected from the group consisting of anionic surfactants, cationic surfactants, amphoteric surfactants, and mixtures thereof,
      (ii) from about 0.1% to about 10% of a charged polymer which has an opposite charge as the surfactant if an amphoteric surfactant is not present either by itself or combined with another surfactant; and
      (iii) from about 80% to about 99% of one or more aqueous carriers;
   wherein the charged polymer is diluted to form a charged polymer slurry and the pH of the charged polymer slurry is from about 1.5 to about 10, the charged polymer slurry is combined with the anionic, cationic, or amphoteric surfactant to form a coacervate gel which is not a microcapsule, and the coacervate gel is then combined with the one or more aqueous carriers to form the dentifrice composition; and
   b. a second dentifrice composition.

2. The dentifrice formulation according to claim 1 wherein the first dentifrice composition further comprises a flavor system, the flavor system being emulsified with the surfactant before the coacervate gel is formed.

3. The dentifrice formulation according to claim 1 wherein the charged polymer is an anionic polymer and the polymer slurry has a pH of from about 1.5 to about 7.

4. The dentifrice formulation according to claim 3 wherein the charged polymer is a carboxyvinyl polymer.

5. The dentifrice formulation according to claim 4 wherein the surfactant is an amphoteric surfactant and an anionic surfactant.

6. The dentifrice formulation according to claim 5 wherein the amphoteric surfactant is cocoamidopropyl betaine and the anionic surfactant is sodium alkyl sulfate.

7. The dentifrice formulation according to claim 6 wherein the first dentifrice composition, the second dentifrice composition, or both of the dentifrice compositions further comprise a soluble fluoride source capable of providing from about 50 ppm to about 3500 ppm of free fluoride ions.

8. The dentifrice formulation according to claim 7 wherein the soluble fluoride source is sodium fluoride.

9. The dentifrice formulation according to claim 8 wherein the first dentifrice composition, the second dentifrice composition, or both of the dentifrice compositions further comprise an effective amount of one or more tartar control agents selected from the group consisting of polyphosphates, pyrophosphate salts, sodium tripolyphosphate, and mixtures thereof.

10. The dentifrice formulation according to claim 9 wherein the first dentifrice composition, the second dentifrice composition, or both of the dentifrice compositions further comprise an effective amount of one or more antimicrobial agents selected from the group consisting of zinc salts, triclosan, chlorhexidine, cetyl pyridinium chloride, and mixtures thereof.

11. The dentifrice formulation according to claim 10 wherein the aqueous carriers are materials selected from the group consisting of alkali metal bicarbonate salts, calcium peroxide, abrasive polishing materials, propylene glycol, acidic compounds, buffering agent, polyoxyethylene, thickening materials, humectants, water, surfactants, titanium dioxide, coolants, sweetening agents, xylitol, coloring agents, and mixtures thereof.

12. The dentifrice formulation according to claim 11 wherein the first dentifrice composition is a dentifrice in the form of a gel and the second dentifrice composition is a dentifrice in the form of a paste.

13. The dentifrice formulation according to claim 1 wherein the charged polymer is a cationic polymer and the polymer slurry has a pH of from about 7 to about 10.

14. An dentifrice formulation contained in physically separated compartments of a dispenser, comprising:
   a. a first dentifrice composition comprising:
      (i) from about 0.1% to about 10% of a surfactant selected from the group consisting of anionic surfactants, cationic surfactants, amphoteric surfactants, and mixtures thereof;
      (ii) from about 0.1% to about 10% of a charged polymer which has an opposite charge as the surfactant if an amphoteric surfactant is not present either by itself or combined with another surfactant;
      (iii) from about 0.001% to about 5% of a flavor system;
      (iv) from about 0.1% to about 30% of a buffering agent; and
      (v) from about 45% to about 99% of one or more aqueous carriers; wherein the charged polymer is diluted to form a charged polymer slurry and the pH of the charged polymer slurry is from about 1.5 to about 10, the flavor system is emulsified with the surfactant, the charged polymer slurry is combined with the emulsified surfactant and flavor system to form a coacervate gel which is not a microcapsule, and the coacervate gel is then combined with the buffering agent and one or more aqueous carriers to form the dentifrice composition; and b. a second dentifrice composition comprising:
  (i) from about 0.1% to about 40% of sodium bicarbonate;
  (ii) an effective amount of one or more tartar control agents selected from the group consisting of polyphosphates, pyrophosphate salts, sodium tripolyphosphate, and mixtures thereof; and
  (iii) from about 50% to about 99% of one or more aqueous carriers.

15. A dentifrice formulation comprising:
  a. from about 0.1% to about 10% of a surfactant selected from the group consisting of anionic surfactants, cationic surfactants, amphoteric surfactants, and mixtures thereof;
  b. from about 0.1% to about 10% of a charged polymer which has an opposite charge as the surfactant if an amphoteric surfactant is not present either by itself or combined with another surfactant; and
  c. from about 80% to about 99% of one or more aqueous carriers; wherein the charged polymer is diluted to form a charged polymer slurry and the pH of the charged polymer slurry is from about 1.5 to about 10, the charged polymer slurry is combined with the anionic, cationic, or amphoteric surfactant to form a coacervate gel which is not a microcapsule, and the coacervate gel is then combined with the one or more aqueous carriers to form the dentifrice composition.

16. A method of making a dentifrice composition containing a coacervate gel, comprising the steps of:
  a. diluting from about 0.1% to about 10% of a charged polymer to form a charged polymer slurry, the charged polymer slurry having a pH of from about 1.5 to about 10;
  b. combining the charged polymer slurry with from about 0.1% to about 10% of a surfactant selected from the group consisting of anionic surfactants, cationic surfactants, amphoteric surfactants, and mixtures thereof, wherein the charged polymer has an opposite charge as the surfactant is an amphoteric surfactant is not present either by itself or combined with another surfactant to form a coacervate gel which is not a microcapsule; and
  c. combining the coacervate gel with from about 80% to about 99% of one or more aqueous carriers to form the dentifrice composition.

17. The method of making a dentifrice composition according to claim 16 wherein the dentifrice composition further comprises a flavor system, the flavor system being emulsified with the surfactant before the coacervate gel is formed.

18. A method of making a dentifrice composition containing a coacervate gel, comprising the steps of:
  a. diluting from about 0.1% to about 10% of a charged polymer to form a charged polymer slurry, the charged polymer slurry having a pH of from about 1.5 to about 10;
  b. emulsifying from about 0.001 to about 5% of a flavor system with from about 0.1% to about 10% of a surfactant selected from the group consisting of anionic surfactants, cationic surfactants, amphoteric surfactants, and mixtures thereof wherein the charged polymer has an opposite charge as the surfactant is an amphoteric surfactant is not present either by itself or combined with another surfactant;
  c. combining the charged polymer slurry with the surfactant and flavor emulsion to form a coacervate gel which is not a microcapsule;
  d. neutralizing the coacervate gel by combining the coacervate gel with from about 0.1% to about 30% of a buffering agent; and
  e. combining the neutralized coacervate gel with from about 45% to about 99% of one or more aqueous carriers to form the dentifrice composition.

* * * * *